United States Patent [19]

Habenstein

[11] Patent Number: 4,481,295
[45] Date of Patent: Nov. 6, 1984

[54] SUBSTITUTED OR CONDENSED PYRIDINES IN A PROCESS FOR THE DETECTION OF SUBSTANCES HAVING A PEROXIDATIC EFFECT AND A DIAGNOSTIC AGENT CONTAINING SUCH PYRIDINES

[75] Inventor: Klaus Habenstein, Lahntal, Fed. Rep. of Germany

[73] Assignee: Behringwerke Aktiengesellschaft, Marburg an der Lahn, Fed. Rep. of Germany

[21] Appl. No.: 163,691

[22] Filed: Jun. 27, 1980

[30] Foreign Application Priority Data

Jun. 29, 1979 [DE] Fed. Rep. of Germany ....... 2926271

[51] Int. Cl.³ .................... G01N 33/52; G01N 33/72; G01N 21/78

[52] U.S. Cl. ...................................... 436/66; 422/56; 435/28; 436/904

[58] Field of Search .............. 23/230 B, 932; 252/408; 435/28; 436/66, 904; 422/56

[56] References Cited

U.S. PATENT DOCUMENTS 3,917,452  11/1975  Rittersdorf et al. .............. 23/230 B
4,251,223  2/1981   White .............................. 23/932 X Primary Examiner—Arnold Turk
Attorney, Agent, or Firm—Curtis, Morris & Safford

[57] ABSTRACT

What are disclosed are a method for detecting substances having a peroxidative effect using a substituted or condensed pyridine, and a diagnostic agent containing a pyridine of this kind.

9 Claims, No Drawings

SUBSTITUTED OR CONDENSED PYRIDINES IN A PROCESS FOR THE DETECTION OF SUBSTANCES HAVING A PEROXIDATIC EFFECT AND A DIAGNOSTIC AGENT CONTAINING SUCH PYRIDINES

The invention relates to the use of substituted or condensed pyridines in a process for the detection of substances having a peroxidative effect and to a pertinent process, and especially to an agent for increasing the sensitivity of the detection of substances having a peroxidative effect, which agent is used above all in a diagnostic agent comprising a carrier, a chromogen, a hydroperoxide, a stabilizer, a detergent and an activator.

The detection of substances having a peroxidative effect, which include hemoglobin and myoglobin in the animal organism, is of high importance for the discovery of small amounts of blood invisible to the eye in body fluids such as urine, or in other excrements, for example feces or vomited matter. In the case of a microscopic hematuria, a high sensitivity, besides the ready availability of the result, is a decisive factor for supporting the blood detection. In tests to increase the sensitivity by adding activating substances to the detection system, it has been found already in 1928 (Zschr. f. gerichtl. Med. 12, 216 (1928)) that quinoline, isoquinoline and derivatives thereof accelerate the detection.

Based on these findings, further quinoline and isoquinoline derivatives have been tested in later years and have been considered suitable (German Auslegeschrift No. 1,242,905, German Offenlegungsschrift No. 2,640,211, German Offenlegungsschrift No. 2,548,279, German Pat. No. 2,235,152). Certain pyridine derivatives have likewise been found to be effective accelerators (German Pat. No. 2,363,344). Thiazole and benzothiazole derivatives represent a further class of substances with accelerating effect (German Offenlegungsschrift No. 2,652,545). Substances of this kind are employed especially in the preparation of rapid diagnostic agents (for example test strips).

Surprisingly, it has now been found that besides the known vinyl pyridines, benzothiazoles or benzopyridines, all heteroaromatic hydrocarbons with at least one nitrogen atoms in the nucleus are in principle suitable accelerators. In this connection, phenyl-, benzyl- and benzoyl pyridines have proved to be novel accelerators having a high efficiency. The efficiency and stability values correspond to those of the vinyl pyridines of German Auslegeschrift No. 2,363,344. A surprising increase in the stability and efficiency is found, if a second bond between the phenyl and the pyridine nucleus is present in the above-mentioned compounds.

The subject of the invention are agents for increasing the sensitivity of the detection of substances having a peroxadative effect, which agents consist partially or totally of a compound of the formula I

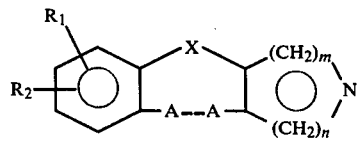

or a salt thereof in which X is $CH_2$, $CHR_1$, $CR_1R_2$, $C=O$ or ⌒X⌒ represents a bond between the two nuclei, m and n represent an integer from 0 to 3, m+n being 3, and if X stands for $C=O$ or ⌒X⌒ is a bond between the two nuclei, each A is a hydrogen atom, and—if X is $CH_2$, $CHR_1$ or $CR_1R_2$—each A is hydrogen or both —A together represent a bond between the two nuclei, and in which $R_1$ and $R_2$ are hydrogen, halogen or alkyl of from 1 to 4 carbon atoms.

The symbols preferably have the following meanings:
X is $CH_2$.
$R_1$ and $R_2$ are hydrogen.
—A—A— represent a bond.

Preference is given in particular to "azafluorenes" or "indenopyridines".

The agent of the invention is preferably employed in a diagnostic agent which consists of a solid carrier material in the form of a strip, preferably of plastic material, onto which a water-absorbing test field has been applied which contains an accelerator of the formula I in addition to buffer salts, hydroperoxide, chromogen, stabilizers and surface-active substances.

Test strips prepared with the accelerators of the invention react very sensitively to the smallest amounts of hemoglobin: in this manner it is possible to detect microscopic hematurias up to 0.03 mg of hemoglobin/l of urine ($=1-2$ erythrocytes/$\mu$l of urine).

By adding one of the known stabilizers (for example hydroquinone, ascorbic acid), the stability of the chemical system may be further increased, while the sensitivity is reduced. The resulting increase of the indication threshold to about 5 erythrocytes/$\mu$l or urine is desirable for screening tests, since generally microscopic hematurias are considered to be pathological only with more than 2 to 3 erythrocytes per $\mu$l being present.

Suitable buffers are, for example citrates, phosphates or phthalates which produce a pH value of from 4 to 7, preferably from 5 to 6, when the test field is moistened.

Suitable hydroperoxides are, for example, cumene-, tetralin-, decalin- or pinane hydroperoxide. As chromogens, benzidine derivatives, preferably the non-carcinogenic tetramethyl benzidine, may be used for example.

Stabilizers of the type of ethylene diamino-tetraacetic acid protect the hydroperoxide by catching heavy metal traces, and thickeners of the gelatin or polyvinyl pyrrolidone type stabilize the chromogen and prevent an excess bleeding of the moistened test field.

Examples for further stabilizers have been indicated in German Pat. No. 2,235,127, U.S. Pat. Nos. 4,071,317 or 4,071,318. Detergents are surface-active substances, such as sodium dodecyl sulfonate or dioctyl sodium-sulfosuccinate.

The water-absorbing test field may in principle consist of any material. There are generally used fiber fleeces of cellulose or plastic material, preferably filter paper. However, there have also been known systems in which non-fibrous materials are used, the chemicals being contained in a water-absorbing film.

The following Examples serve to illustrate the invention.

EXAMPLE 1

| Solution 1 | 300 mg of polyvinyl pyrrolidone, |
|---|---|
| | 10 mg of EDTA-di-sodium salt, |
| | 7.5 mg of tartrazine, |
| | 20 mg of dioctyl sulfosuccinate-Na salt, |
| | 20 mg of 4-azafluorene, |
| | 2.2 mmols of citric acid and |
| | 30 mg of 3,3',5,5'-tetramethyl benzidine |
| | are dissolved in |

-continued

| 6 ml of methanol and |
| 4 ml of water. |

The pH value is adjusted to 5.5.

| Solution 2 | 60 mg of decalin hydroperoxide are dissolved in 10 ml of toluene. |

100 cm² of filter paper are impregnated with solution 1 and after drying with solution 2.

After having been dried again, the paper clearly indicates a hemoglobin concentration of about 0.14 mg of Hb/liter of urine by a green discoloration (corresponding to about 5 erythrocytes/μl).

EXAMPLE 2

| 300 mg of polyvinyl pyrrolidone, |
| 10 mg of EDTA-di-sodium salt, |
| 7.5 mg of tartrazine, |
| 20 mg of dioctyl sulfosuccinate-sodium salt, |
| 2.2 mmols of citric acid, |
| 250 mg of cumene hydroperoxide, |
| 30 mg 3,3',5,5'-tetramethyl benzidine and |
| 20 mg of 4-azafluorene are dissolved in |
| 6 ml of methanol and |
| 4 ml of water. |

The pH value is adjusted to 5.5.

100 cm² of filter paper are impregnated with this solution and dried.

The finished paper makes it possible to detect 0.03 mg of Hb/liter of urine (corresponding to about 1-2 erythrocytes/μl of urine) by a green discoloration of the paper, i.e. 1 to 2 intact erythrocytes/μl of urine are marked as clear green dots on the otherwise yellow background.

If the 4-azafluorene is replaced by 20 mg of 2-benzyl pyridine, 2-phenyl pyridine or 9-bromo-4-azafluorene, the sensitivity of the test papers corresponds to that of Example 1. If said 4-azafluorene is replaced by 20 mg of 2-, 3-, or 4-benzoyl pyridine or 3- or 4-benzyl pyridine, the sensitivity of the test papers corresponds to an indication of 5 to 10 erythrocytes per/μl of urine.

EXAMPLE 3

| 300 mg of polyvinyl pyrrolidone, |
| 10 mg of EDTA-di-sodium salt, |
| 7.5 mg of tartrazine, |
| 20 mg of dioctyl sulfosuccinate-sodium salt, |
| 2.2 mmols of citric acid, |
| 250 mg of cumene hydroperoxide, |
| 30 mg of 3,3',5,5'-tetramethyl benzidine and |
| 20 mg of 4-azafluorene are dissolved in |
| 6 ml of methanol and a solution of |
| 200 μg of ascorbic acid in |
| 4 ml of H₂O. |

The pH value is adjusted to 5.5.

100 cm² of filter paper are impregnated with this solution and dried. The detection sensitivity of the finished paper is comparable with that of the paper of Example 1.

What is claimed is:

1. A method for detecting a substance having a peroxidative effect, which method comprises contacting said substance with a hydroperoxide and a chromogen in the presence of an activator which is a compound of the formula

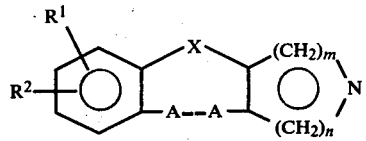

or a salt thereof, wherein
X is $-CH_2-$, $-CHR_1-$, $-CR_1R_2-$, $=C=O$, or a chemical bond,
m and n are each an integer from 0 to 3 inclusive and $m+n=3$;
A is hydrogen if X is $=C=O$ or a chemical bond and A is hydrogen or a chemical bond if X is $-CH_2-$, $-CHR_1-$, or $-CR_1R_2-$; and
$R_1$ and $R_2$ are hydrogen, halogen, or alkyl having 1 to 4 carbon atoms,
whereby a color change in said chromogen is indicative of the presence of such a substance having a peroxidative effect.

2. A method as in claim 1 wherein said activator is 4-azafluorene.

3. A diagnostic agent for detecting a substance having a peroxidative effect, which agent comprises a chromogen, a hydroperoxide, an activator, and a carrier therefor, said activator being a compound of the formula

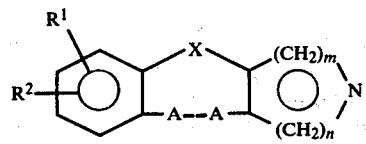

or a salt thereof, wherein
X is $-CH_2-$, $-CHR_1$, $-CR_1R_2-$, $=C=O$, or a chemical bond;
m and n are each an integer from 0 to 3 inclusive and $m+n=3$;
A is hydrogen if X is $=C=O$ or a chemical bond and A is hydrogen or a chemical bond if X is $-CH_2-$, $-CHR_1$, or $-CR_1R_2-$; and
$R_1$ and $R_2$ are hydrogen, halogen, or alkyl having 1 to 4 carbon atoms.

4. A diagnostic agent as in claim 3 wherein said activator is 4-azafluorene.

5. A diagnostic agent as in claim 3 which additionally comprises a stabilizer and a detergent.

6. A test composition for detection of peroxidatively active substances comprising an indicator capable of being oxidized in the presence of a peroxidatively active substance to provide a color change, an oxidizing agent effective to oxidize said indicator, and 4-azafluorene as a sensitizing agent.

7. A test device for detection of peroxidatively active substances which comprises a carrier incorporated with the composition of claim 6.

8. A process for preparing a device for the determination of peroxidatively active substances which comprises incorporating a carrier with the composition of claim 6.

9. A method for the determination of peroxidatively active substances in a sample which comprises contacting said sample with the composition of claim 6 and observing any resultant color change.

* * * * *